United States Patent [19]

Sasaki et al.

[11] 4,295,855
[45] Oct. 20, 1981

[54] METHOD FOR SEPARATING FIBRINOGEN AND ITS CONSTITUENT COMPONENTS

[75] Inventors: Susumu Sasaki, Nagoya; Kyoji Kito, Seto; Akio Koide, Ichinomiya, all of Japan

[73] Assignees: Meito Sangyo Kabushiki Kaisha; Susumu Sasaki, both of Aichi, Japan

[21] Appl. No.: 110,946

[22] Filed: Jan. 10, 1980

[30] Foreign Application Priority Data

Jan. 16, 1979 [JP] Japan .................................. 54/2162

[51] Int. Cl.³ .................. G01N 33/50; G01N 33/68
[52] U.S. Cl. ............................. 23/230 B; 252/408; 260/112 B
[58] Field of Search ............ 23/230 B; 260/112 B; 252/408

[56] References Cited

U.S. PATENT DOCUMENTS 4,066,549  1/1978  Oeser ........................... 260/112 B
4,085,095  4/1978  Bick ............................. 260/112 B
4,188,318  2/1980  Shanbrom ..................... 260/112 B

OTHER PUBLICATIONS

G. F. Grannis, Clinical Chemistry, 16 (6), 486–494 (1970).
K. Yamado et al., Clincal Blood, 13, 411–414 (1972).
M. B. Garvey et al., J. Clin. Path., 25, 680–682 (1972).
M. Fujimaki et al., Blood and Vessels, 5, 1015–1020, (in Japanese and in English), (1974).
O. H. Lowry et al., J. Biol Chem., 193, 265–275 (1951).
Von A. Clauss, Acta. Hoemat., 17, 237–246, (in German), (1957).
B. C. Ellis et al., J. Lab. Clin. Med., 58, 477–488 (1961).
E. J. Hershgold et al., A. J.C.P., 63, 231–236 (1975).
Chemical Abstracts, 86:12949e (1977).
I. Lipinska et al., J. Lab. Clin. Med., 84 (4), 509–516 (1974).
J. S. Finlayson et al., Biochemistry, 2 (1), 42–46 (1963).
L. A. Kazal et al., P.S.E.B.M., 113, 989–994 (1963).

Primary Examiner—Sidney Marantz
Attorney, Agent, or Firm—Sherman & Shalloway

[57] ABSTRACT

A method for obtaining fibrinogen or its constituent components, which comprises contacting a fibrinogen-containing composition with at least one aminocarboxylic acid of the formula $$H_2N(CH_2)_nCO_2H$$

wherein n is a positive integer, in an aqueous medium in the presence of an ionic strength controlling agent to collect at least one member selected from the group consisting of, fibrinogen fraction 1 and fibrinogen fraction 2; a method for determining fibrinogen in plasma, sample for assaying fibrin degradation products and fibrinogen degradation products, and a reagent for obtaining or determining fibrinogen or its components.

14 Claims, 16 Drawing Figures

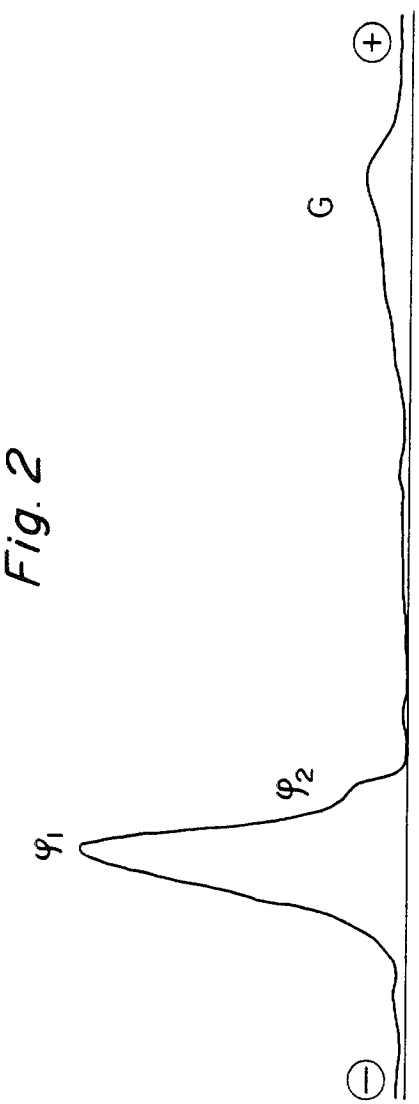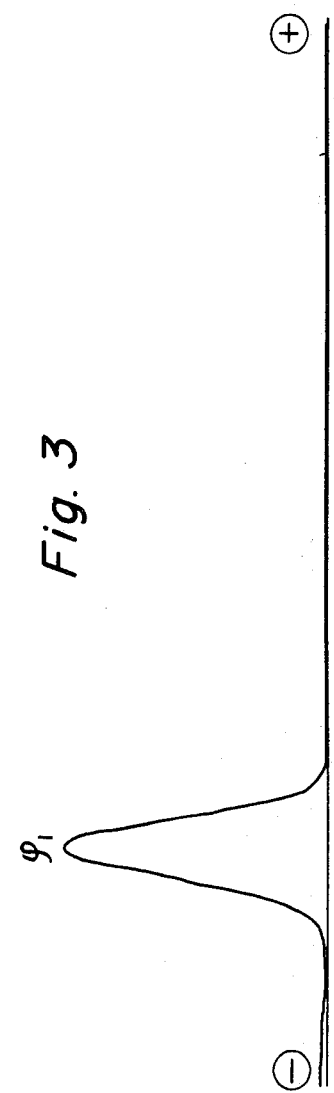

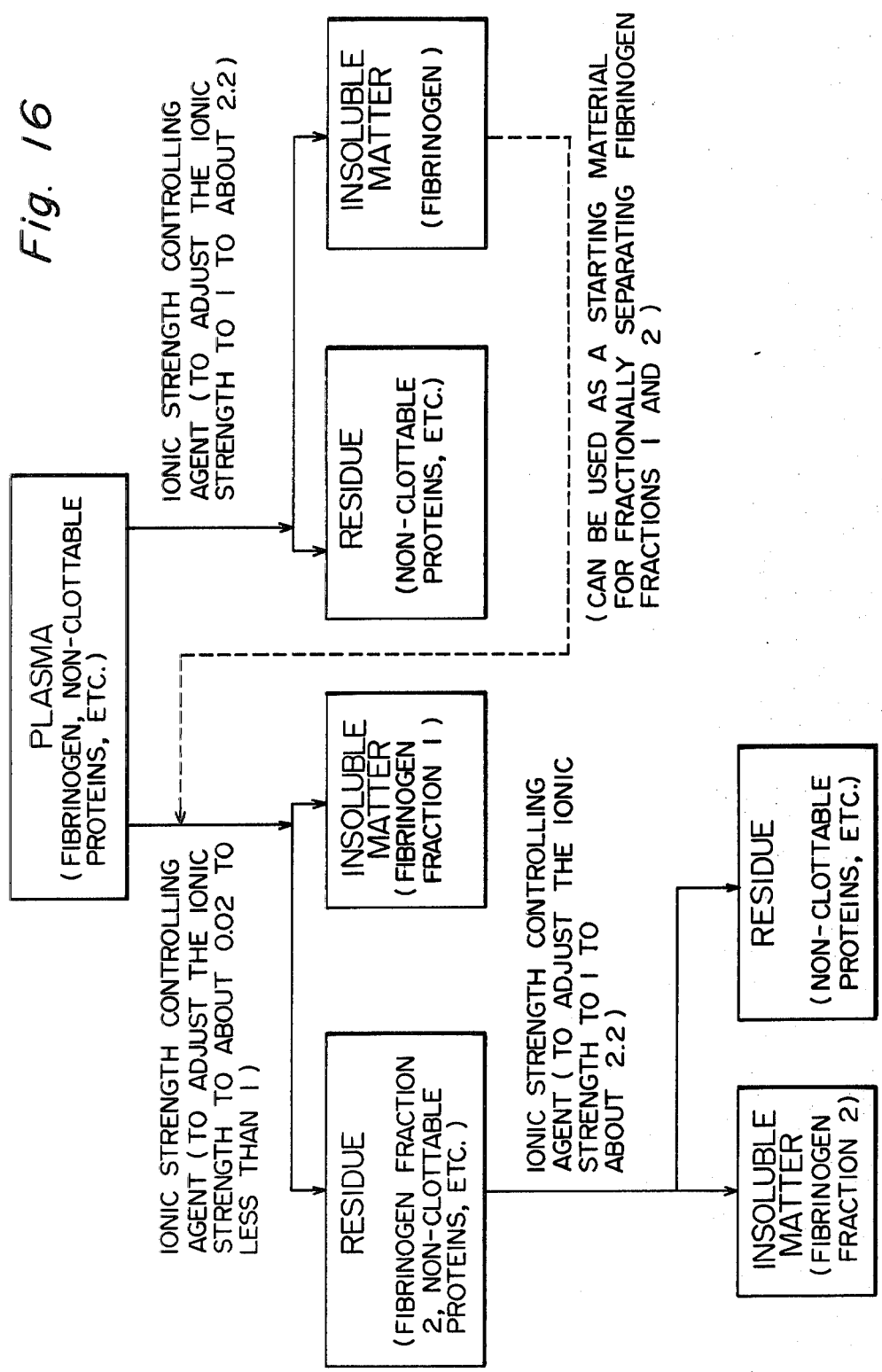

METHOD FOR SEPARATING FIBRINOGEN AND ITS CONSTITUENT COMPONENTS

This invention relates to a method for obtaining high-purity fibrinogen and fibrinogen fractions 1 and 2, its constituent components, selectively and easily with high accuracy by removing impurities including non-clottable proteins from an aqueous solution containing fibrinogen, such as plasma, using a simple operation. It also relates to a method for determining fibrinogen, fibrinogen fraction 1 or fibrinogen fraction 2 in plasma easily and rapidly with high accuracy and reliability to provide information beneficial to the diagnosis of liver diseases and diseases induced by coagulation disorders of blood such as hemorrhagic diseases, thromobosis, and DIC syndrome (intravascular coagulation syndrome).

This invention further relates to the use of a residual liquid left after the separation of fibrinogen by the aforesaid method as a sample for assaying fibrin and fibrinogen degradation products (to be referred to as FDP).

Furthermore, the invention relates to reagents required for the practice of the aforesaid methods for obtaining or determining fibrinogen or its consituent components.

Fibrinogen is a protein existing in normal plasma. Under the action of thrombin enzyme, fibrinogen polymerizes to insoluble macromolecular fibrin fibers constituting an important component of blood clot. It is a glucoprotein produced mainly in the liver and having a molecular weight of about 340,000. The fibrinogen molecule consists of three polypeptide chains, $A\alpha$, $B\beta$ and $\gamma$. Fibrinogen has been considered to be a single protein, but recent works have shown that it consists of at least two constituent components.

For example, Lipinska et al. showed by SDS-polyacrylamide gel electrophoresis that fibrinogen in normal human plasma consists of a high-molecular-weight component (fibrinogen fraction 1) and a low-molecular-weight component (fibrinogen fraction 2), and suggested the possibility that the ratio between these fractions would affect the physiological function of fibrinogen [I. Lipinska et al., J. Lab. Clin. Med., 84, (4), 509–516 (1974)].

Finlayson et al. discovered that human fibrinogen having a purity of 98% is separated into two peaks by column chromatography on a DEAE-cellulose column [J. S. Finlayson et al., Biochemistry, 2 (1), 42–46 (1963)].

An important physiological function of fibrinogen is that exhibited in the coagulation of blood, as stated above. When a blood coagulating mechanism begins to work, hydrolase thrombin appears in the plasma, and fibrinogen is partly degraded at its specified position by the action of the enzyme to a fibrin monomer. The fibrin monomer then polymerizes to fibrin fibers to form a blood clot. In other words, the essence of blood coagulation is the conversion of fibrinogen to fibrin. It is very significant therefore to know the quantity and quality of plasma fibrinogen for the diagnosis of liver diseases and the diseases caused by coagulation disorders of blood exemplified hereinabove.

From the standpoint of clinical medicine, it is desired to determine fibrinogen easily and rapidly with high accuracy and reliability.

Conventional assay methods used in clinical application, however, are based on the assumption that fibrinogen is a single protein, and no effort has been made to know the individual amounts of fibrinogen fractions 1 and 2. None of the conventional assay methods clinically employed have been able to detect the amounts of the individual components of fibrinogen. Moreover, the conventional methods of determination have other defects and can scarcely realize the above desire. For example, a long period of time is required for determination. Or because fibrinogen containing fairly large amounts of impurities is determined, the error of determination is great, and the accuracy and reliability of these methods are low. Furthermore, these methods cannot make use of an autoanalyzer which is operationally advantageous. Or the operation is complicated in these methods.

For example, the Folin-Lowry method previously employed as a standard method of determination has the disadvantage that its operation is complicated, and a period of as long as about 3 hours is required. Another defect is that fragment X, which is a degradation product of fibrin and fibrinogen, is also determined as fibrinogen. A thrombin time method can effect determination relatively rapidly, but with a blood sample containing a significant amount of anti-thrombin, the error of determination increases and the accuracy and reliability of assay are reduced. An ammonium sulfate nephelometric method can effect determination relatively rapidly, but results in measuring considerable amounts of non-clottable proteins as fibrinogen, thus causing poor accuracy and reliability. Furthermore, the conventional methods, except the nephelometric method utilizing an immuniological reaction, have the inconvenience that autoanalyzers cannot be utilized.

It is known, on the other hand, that aminocarboxylic acids such as glycine, $\beta$-alanine, $\gamma$-aminobutyric acid and $\epsilon$-aminocaproic acid precipitate fibrinogen. For example, Kazal et al. reported that fibrinogen having a clottability (the percentage of a thrombin-clottable protein based on total proteins) of 94.4% was obtained by adding barium sulfate to human plasma to remove prothrombin in advance, adding a glycine powder to the supernatant liquid to precipitate fibrinogen, dissolving it in an aqueous solution of sodium citrate having a pH of 7.4, and then repeating the precipitation with glycine several times [L. A. Kazal et al., PSEBM, 113, 989–994 (1963)]. Such a method, however, is unsuitable for application to the determination of plasma fibrinogen because under these conditions, not all, nor a greater portion, of fibrinogen in the assay sample can be precipitated, thus leaving a significant amount of it unprecipitated. For the fractional determination of fibrinogen fractions 1 and 2, the aforesaid method of Lipinska et al. based on SDS-polyacrylamide gel electrophoresis is available. Great expertise, however, is required for its practice, and two to three days are required until the result is obtained. Such a method can hardly be used in the field of clinical tests which require rapidity and simplicity.

The present inventors made investigations in order to remedy or overcome the many defects or disadvantages of the prior art, and to develop a method which can fractionally give high-purity fibrinogen, fibrinogen fraction 1 or fibrinogen fraction 2 easily and selectively with high accuracy and reliability from a fibrinogen-containing aqueous solution such as plasma.

These investigations led to the discovery that there is a complex correlation between the precipitability of fibrinogen and the chain length and concentration of the aminocarboxylic acid, the ionic strength of the system, the pH of the system, etc. On further investigation, it has been found that by contacting at least one aminocarboxylic acid of the formula

  (I)

wherein n is a positive integer, preferably 1, 2 or 3, with a fibrinogen-containing composition in an aqueous medium in the presence of an ionic strength controlling agent, substantially all the fibrinogen contained in it can be precipitated, almost quantitatively in practical application, without any substantial co-precipitation of proteins other than fibrinogen.

It has also been found that by adjusting the ionic strength of the system with the ionic strength controlling agent, fibrinogen fractions 1 and 2 as constituents of fibrinogen can be fractionally separated and recovered, and that by using the newly developed method for obtaining fibrinogen and fibrinogen fraction 1 or 2, a method for determining these components in a blood sample easily and rapidly with high accuracy and reliability can be provided, thus making it possible to give information for the diagnosis of liver diseases or diseases caused by coagulation disorders of blood with high accuracy, reliability and rapidity.

The inventors have also found that the residue left after removal of fibrinogen is a better sample for determining FDP in blood than conventional ones, and the present invention can make a significant contribution to medical fields in general including physiological, pathological and therapeutic areas.

It is an object of this invention therefore to provide a method for separating high-purity fibrinogen or its constituents from an aqueous solution containing fibrinogen such as plasma, rapidly and selectively by a simple operation.

Another object of this invention is to provide a method for determining by utilizing the aforesaid method the amount of fibrinogen or its constituents in blood plasma with high accuracy, reliability and rapidity, which amount provides information useful for the diagnosis of liver diseases and diseases caused by coagulation disorders of blood.

Still another object of this invention is to provide the use of the residue left after removal of fibrinogen by the aforesaid method as a sample for the determination of FDP in blood.

A further object of this invention is to provide a reagent used to separate or determine fibrinogen or its constituents from or in an aqueous solution containing fibrinogen.

The aforesaid objects and other objects and advantages of this invention will become more apparent from the following description.

According to this invention, at least one aminocarboxylic acid of formula (I) is contacted with a fibrinogen-containing composition in an aqueous medium in the presence of an ionic strength controlling agent to separate fibrinogen or its constituents.

According to one embodiment of obtaining fibrinogen by the method of this invention, an aqueous solution of at least one aminocarboxylic acid of formula (I) is contacted with a fibrinogen-containing aqueous solution, such as plasma, in the presence of an ionic strength controlling agent which is of such a type and in such an amount that the ionic strength of the system (the "ionic strength of the system", as used in the present application, denotes the ionic strength based on all ingredients in the system other than the aminocarboxylic acid, such as the aqueous solution containing fibrinogen, the ionic strength controlling agent, a pH controlling agent, an antiseptic, a stabilizer, etc.; because the proportion of plasma in the system is small and thus the ionic strength of the system which is attributed to the plasma is small, the ionic strength of plasma shall be neglected) is adjusted to 1 to about 2.2, preferably to about 1.1 to about 2, more preferably to about 1.2 to about 1.8. By collecting the insoluble matter formed, high-purity fibrinogen can be obtained easily and selectively.

According to one embodiment of obtaining fibrinogen fraction 1 by the method of this invention, an aqueous solution of at least one aminocarboxylic acid of formula (I) is contacted with a fibrinogen-containing aqueous solution, such as plasma, in the presence of an ionic strength controlling agent which is of such a type and in such an amount that the ionic strength of the system is adjusted to about 0.02 to less than 1, preferably to about 0.03 to about 0.9, more preferably to about 0.1 to about 0.55, and by collecting the insoluble matter formed, high-purity fibrinogen fraction 1 can be easily and selectively obtained.

According to one embodiment of obtaining fibrinogen fraction 2 by the process of this invention, the ionic strength of the residue resulting from the separation of the fibrinogen fraction 1 as the insoluble matter formed by the aforesaid embodiment of obtaining fibrinogen fraction 1 is adjusted to 1 to about 2.2, preferably to 1.1 to about 2, more preferably to about 1.2 to about 1.8 by using an ionic strength controlling agent of such a type and in such an amount that the ionic strength of the system is adjusted to the aforesaid range, and the resulting insoluble matter is collected to obtain high-purity fibrinogen fraction 2 easily and selectively.

In an alternative embodiment of obtaining fibrinogen fraction 1, fibrinogen is first separated by the aforesaid embodiment of obtaining fibrinogen and is re-dissolved in an aqueous medium such as a phosphate buffer or physiological saline, and the solution is used as the fibrinogen-containing aqueous solution. By treating the residue left after the separation of fibrinogen fraction 1 in this alternative embodiment in accordance with the aforesaid embodiment of obtaining fibrinogen fraction 2, fibrinogen fraction 2 can also be obtained.

If desired, in any of the aforesaid embodiments, the insoluble component formed may be separated, and redissolved in the aforesaid aqueous medium, and the solution may be subjected again to a precipitating treatment. This treatment may be repeated a number of times. Such a purifying means can only be used when further purification is necessary, because even without such a purification means, the product obtained by the present invention has a sufficiently high purity.

In the practice of the process of this invention, an aqueous solution of reagent prepared in advance and containing at least one aminocarboxylic acid of formula (I) and an ionic strength controlling agent can be used. It is also possible to use the reagent in solid form, or to add powdery fibrinogen to the aqueous reagent solution in the aforesaid alternative embodiment of obtaining fibrinogen fraction 1.

It should be understood therefore that the contacting of at least one aminocarboxylic acid of formula (I) with the fibrinogen-containing composition in an aqueous medium in the presence of the ionic strength controlling agent in the method of this invention includes not only the aforesaid embodiments, but also an embodimemt in which these ingredients to be contacted are prepared in the form of aqueous solution prior to contacting. In short, it denotes all embodiments in which the aforesaid aminocarboxylic acid, fibrinogen and the ionic strength controlling agent can contact each other as solution in an aqueous medium.

Several examples of the separation of fibrinogen or its constituents from plasma in accordance with this invention are schematically shown in FIG. 16 of the accompanying drawings.

As is shown in FIG. 16, the method of this invention can permit selective and easy separation of substantially all of fibrinogen or fibrinogen fraction 1 or fraction 2 in high purity from plasma, and by utilizing this method, a method for determining fibrinogen or fibrinogen fraction 1 or fibrinogen fraction 2 can be provided.

The aminocarboxylic acid used in the method of this invention is expressed by the general formual $$H_2N(CH_2)_nCO_2H \qquad (I)$$

wherein n is a positive integer, preferably 1, 2 or 3. When n is 1, it is glycine; when n is 2, it is β-alanine, and when n is 3, it is γ-aminobutyric acid. Those of formula (I) in which n is 1 or 2 are preferred.

The contacting is usually carried out at room temperature. But if desired, it may be carried out under cooling or heating, and temperatures in the range of about 10 to about 40° C. can be employed.

Water-soluble electrolytes having the ability to control ionic strength without exerting adverse effects such as denaturation or decomposition on plasma proteins may be widely used as the ionic strength controlling agent in the method of this invention. Examples of preferred ionic strength controlling agents include alkali metal salts and ammonium salts of inorganic or organic acids, such as sodium chloride, potassium chloride, ammonium chloride, sodium sulfate, potassium sulfate, ammonium sulfate, sodium acetate, potassium acetate, ammonium acetate, sodium citrate, potassium citrate, ammonium citrate, potassium phosphate (monobasic), sodium phosphate (dibasic) and ammonium phosphate. Acid salts of alkanolamines such as ethanolamine hydrochloride may also be used. These exemplified electrolytes can be used either singly or as a mixture of two or more. Sodium chloride, potassium chloride, and ammonium sulfate are especially preferred ionic strength controlling agents for use in this invention.

The ionic strength controlling agent may be used in the form of a salt prepared in advance. Alternatively, the salt may be formed in situ in the system in which the fibrinogen-containing composition is contacted with the aminocarboxylic acid, so that the presence of the ionic strength controlling agent in the system is realized.

In contacting the specified aminocarboxylic acid with fibrinogen in the presence of the ionic strength controlling agent in an aqueous medium, it is preferred to adjust the concentration of the aminocarboxylic acid and the pH of the system to suitable ranges in addition to adjusting the ionic strength of the system with the controlling agent to ranges suitable for the desired embodiment. The pH of the system is adjusted to about 5 to about 8, preferably to about 5.5 to about 7.5, more preferably to about 5.7 to about 7.5.

Acids, alkalies and buffers can be used in the aforesaid pH adjustment. Examples include acids such as hydrochloric acid, sulfuric acid, phosphoric acid, acetic acid and citric acid; alkalies such as sodium hydroxide, potassium hydroxide, ammonium hydroxide, sodium hydrogen carbonate and sodium carbonate; and buffers such as acetic acid-sodium acetate, phosphoric acid-sodium phosphate, citric acid-sodium citrate and hydrochloric acid-barbital sodium. These pH controlling agents may be suitably combined to use them as ingredients for the formation of the ionic strength controlling agent.

The concentration of the aminocarboxylic acid is suitably changed according to the type of the aminocarboxylic acid. It is preferably about 1.5 to about 3 M, more preferably about 1.7 to about 2.7 M, especially about 1.9 to about 2.5 M, based on the volume of the system.

The ionic strength of the system in the method of this invention, the concentration of the aminocarboxylic acid in the system and the pH of the system have been examined using normal human plasma as an assay sample, sodium chloride as the ionic strength controlling agent, and glycine as the aminocarboxylic acid.

FIG. 1 of the accompanying drawings shows the relation between the fibrinogen content of precipitated proteins and the ionic strength of a system having a pH of 6.2 and a glycine concentration of 2.1 M while varying the ionic strength of the system with sodium chloride as the ionic strength controlling agent.

FIG. 2 is a densitogram of precipitated proteins determined by SDS-polyacrylamide gel electrophoresis in the system described with regard to FIG. 1 but without using ionic strength controlling agent (i.e., at an ionic strength of 0).

FIG. 3 shows a densitogram, similar to FIG. 2, determined at an ionic strength of 0.2 in the system described with respect to FIG. 1.

Figure 1:
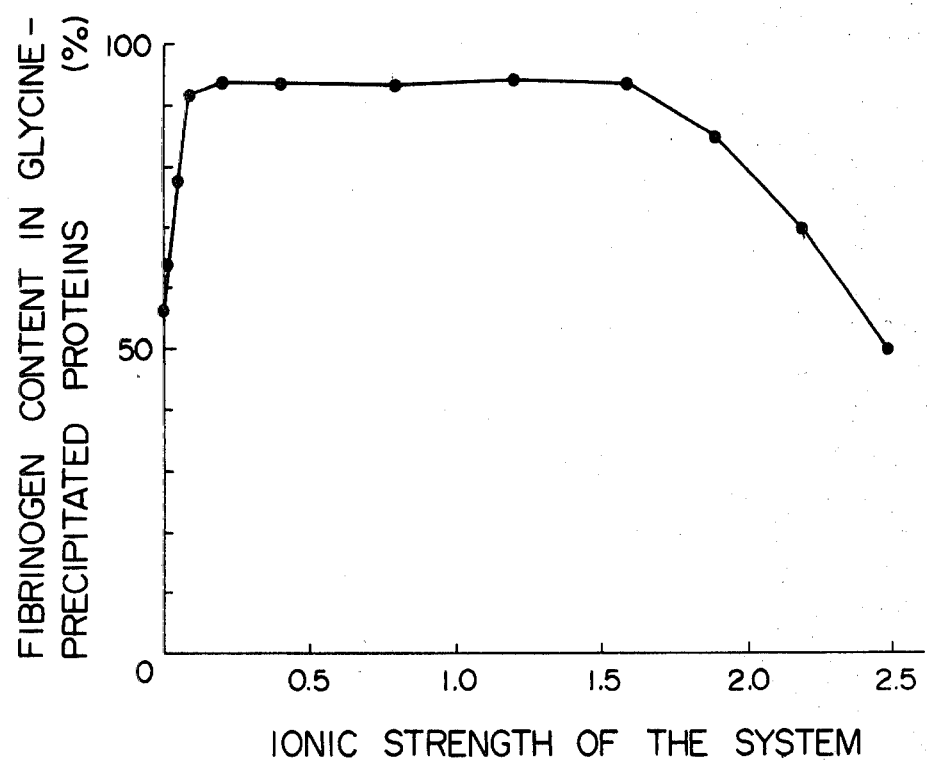

It is seen from FIG. 1 that when the plasma is contacted with glycine in the absence of an ionic strength controlling agent as in the prior art, the fibrinogen content in the resulting precipitate is as low as about 55%, and the precipitate is heavily contaminated by non-clottable proteins.

Furthermore, as shown in FIG. 1, when the ionic strength of the system exceeds 2.2 the fibrinogen content in the precipitate again decreases substantially. For example, at an ionic strength of 2.5, the fibrinogen content in the precipitate is as low as about 50%, showing heavy contamination by non-clottable proteins. It is seen therefore that the ionic strength of the system is advantageously up to about 2, preferably up to 1.8.

Figure 4:
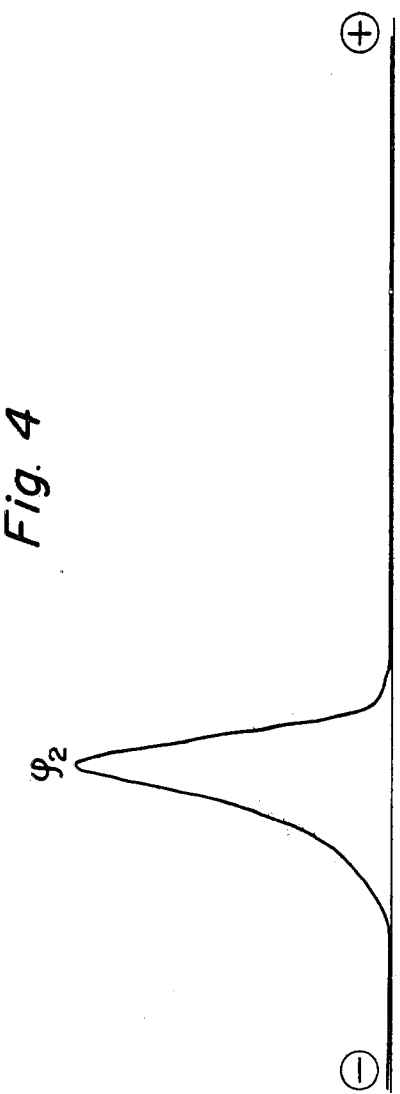
FIG. 4 shows a densitogram, similar to FIG. 2, determined on the residue left after separation of fibrinogen fraction 1 ($\psi_1$ in the figure) in the system described with regard to FIG. 3, the ionic strength of the residue being adjusted to 1.4 with sodium chloride.

It is seen from FIG. 2 that the aforesaid very impure precipitate formed at an ionic strength of 0 contains fibrinogen fractions 1 and 2 (indicated by $\psi_1$ and $\psi_2$) together with non-clottable proteins (shown by G in the drawing). In contrast, according to one embodiment of this invention, fibrinogen fraction 1 in a high purity can be selectively obtained as shown in FIG. 3, and fibrinogen fraction 2 in a high purity can be obtained selectively according to another embodiment of this invention as shown in FIG. 4. It is also seen that as shown in FIG. 5, according to still another embodiment of this invention, fibrinogen in a high purity can be selectively obtained.

Figure 6:
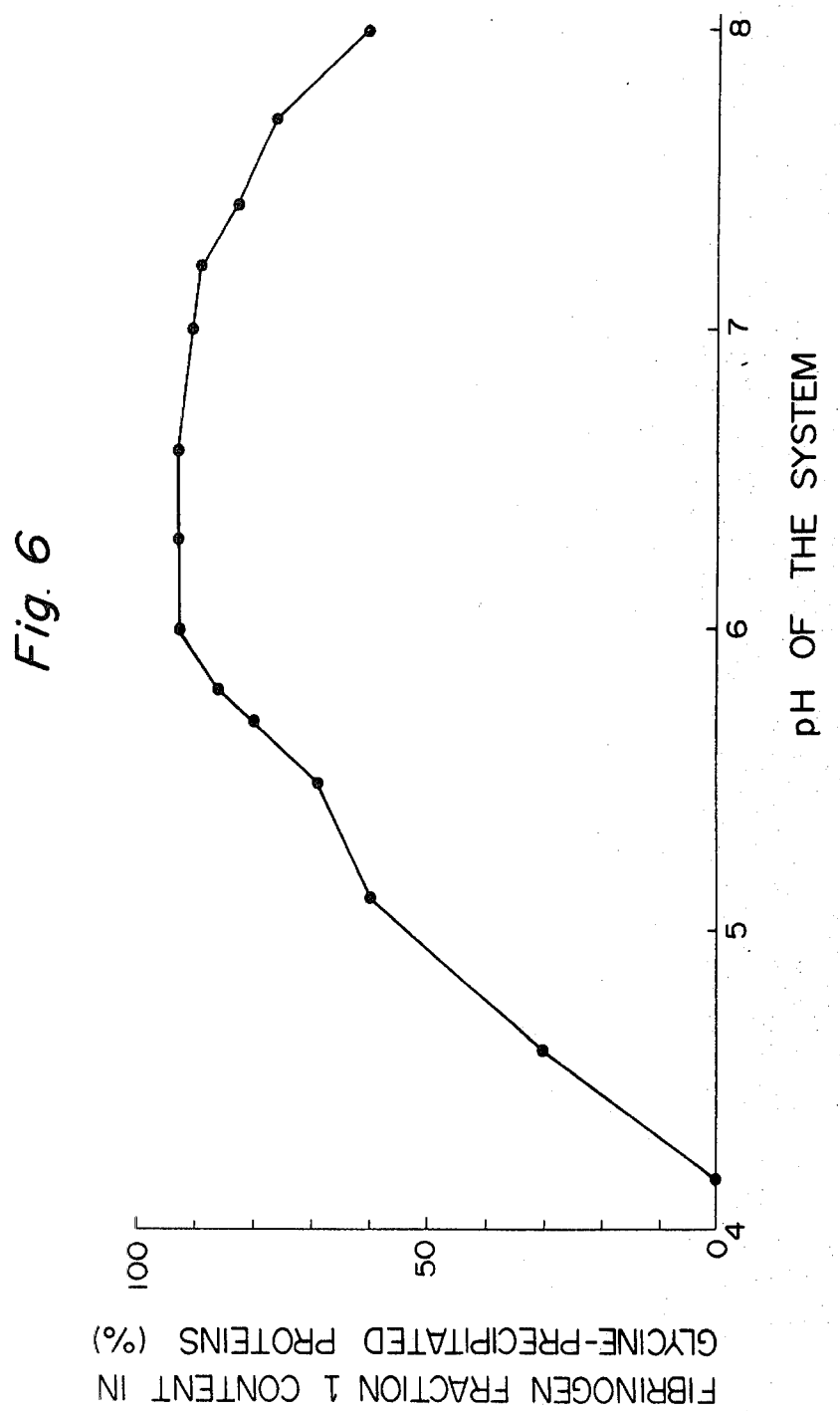

FIG. 6 shows the relation between the content of fibrinogen fraction 1 and the pH of the system determined at an ionic strength of 0.2 as in FIG. 3 while varying the pH of the system.

Figure 7:
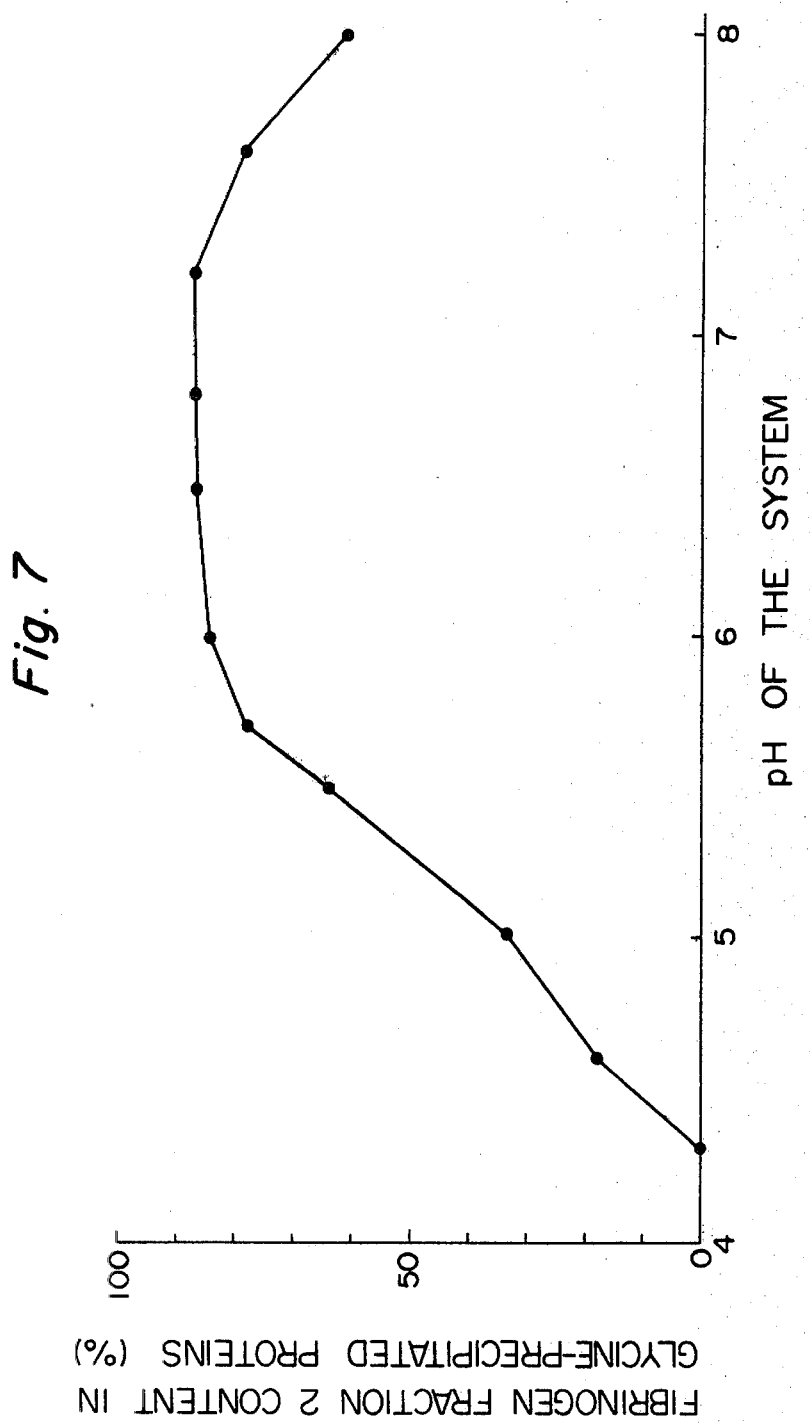

FIG. 7 is a graph, similar to FIG. 6, which shows the relation between the content of fibrinogen fraction 2 and the pH of the system which is determined in the same way as in FIG. 4.

Figure 5:
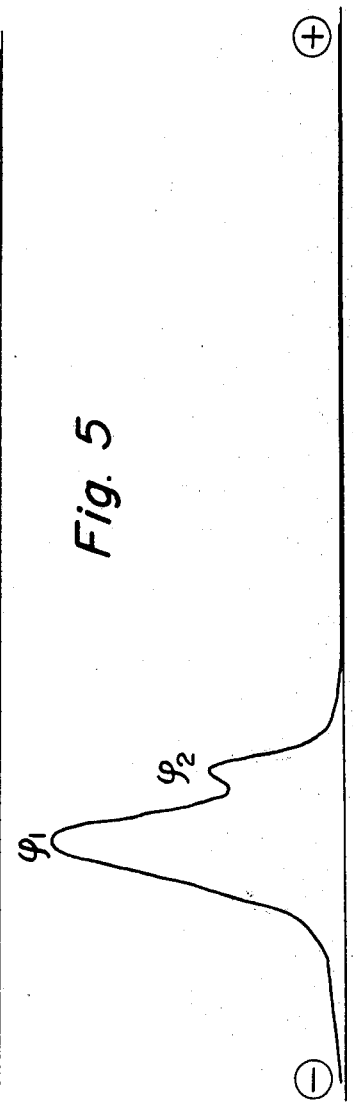
FIG. 5 shows a densitogram, similar to FIG. 2, determined on the system described with regard to FIG. 1 at an ionic strength of 1.4.
Figure 8:
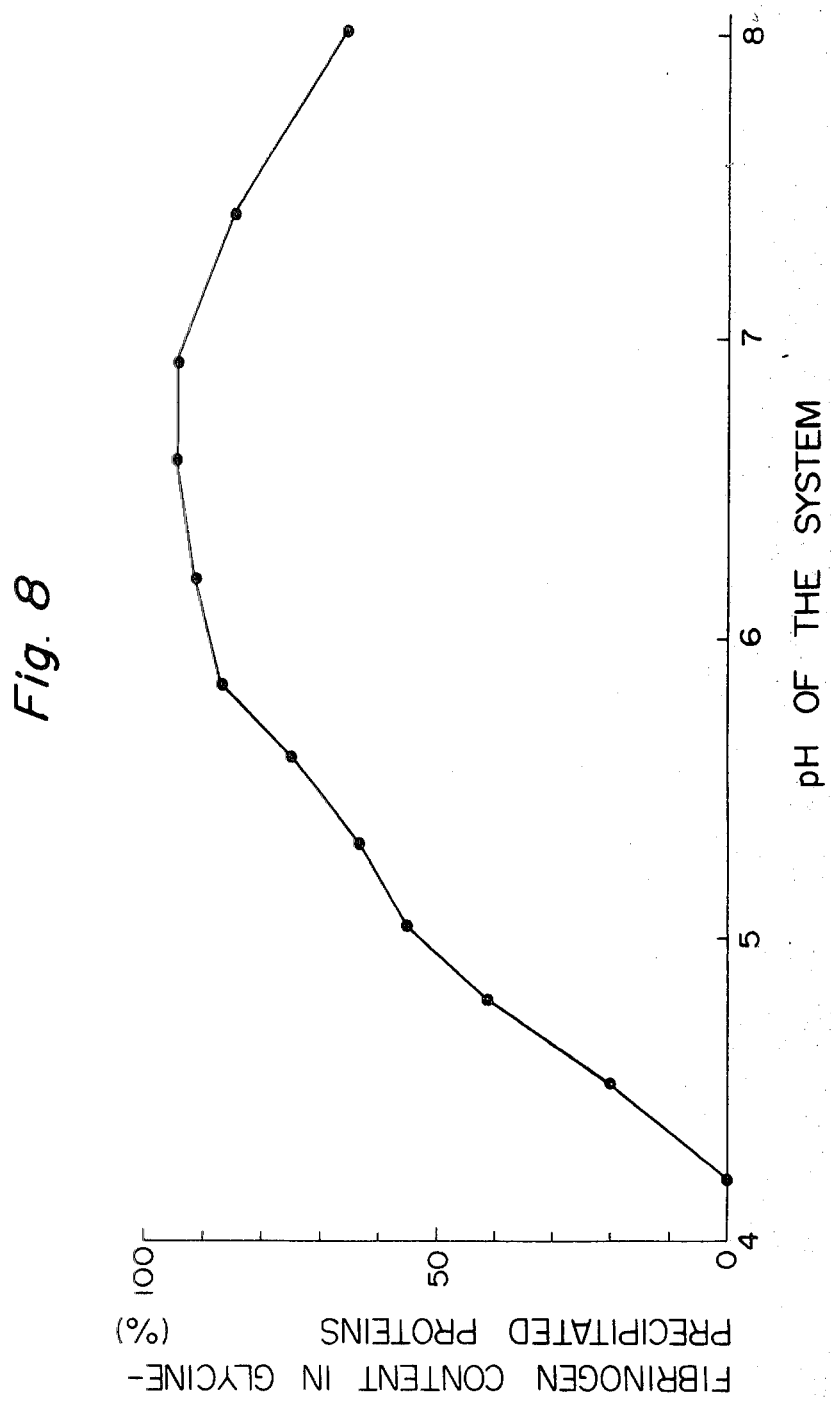

FIG. 8 is a graph, similar to FIG. 6, which shows the relation between the content of fibrinogen (fractions 1 and 2) and the pH of the system which was determined in the same way as in FIG. 5 by varying the pH of the system.

It is seen from the results shown in FIGS. 6 to 8 that it is suitable to adjust the pH of the system to about 5 to about 8, preferably to about 5.5 to about 7.5, especially preferably to about 5.7 to about 7.5.

Figure 9:
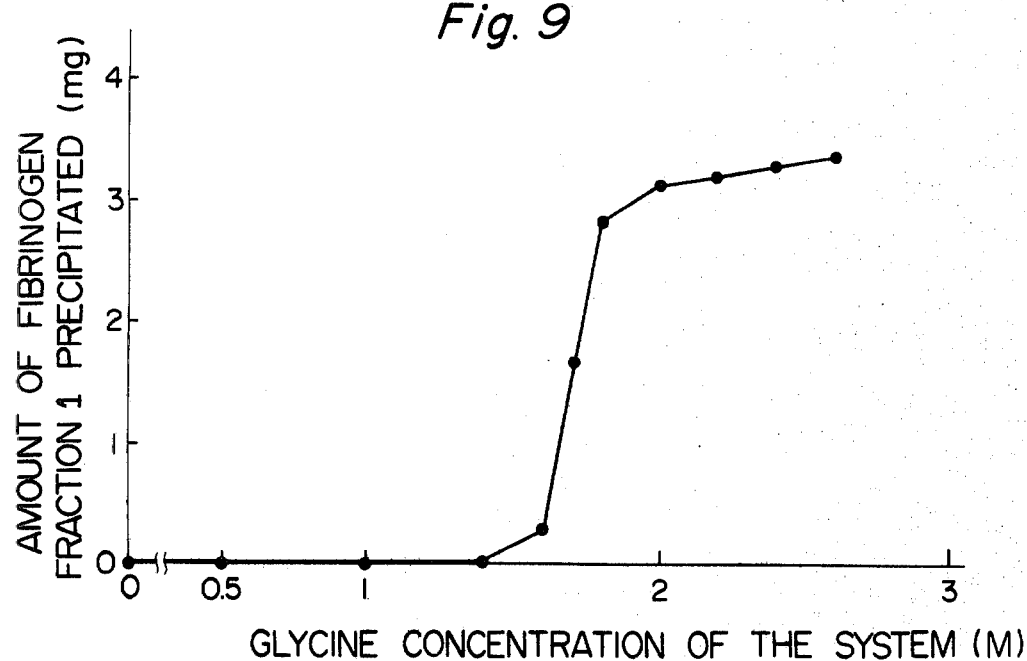

FIG. 9 of the accompanying drawings shows the relation between the amount of fibrinogen fraction 1 precipitated and the concentration of glycine which was determined in the same way as in the case of FIG. 3 by varying the concentration of glycine at a pH of 6.6 and an ionic strength of 0.1.

Figure 10:
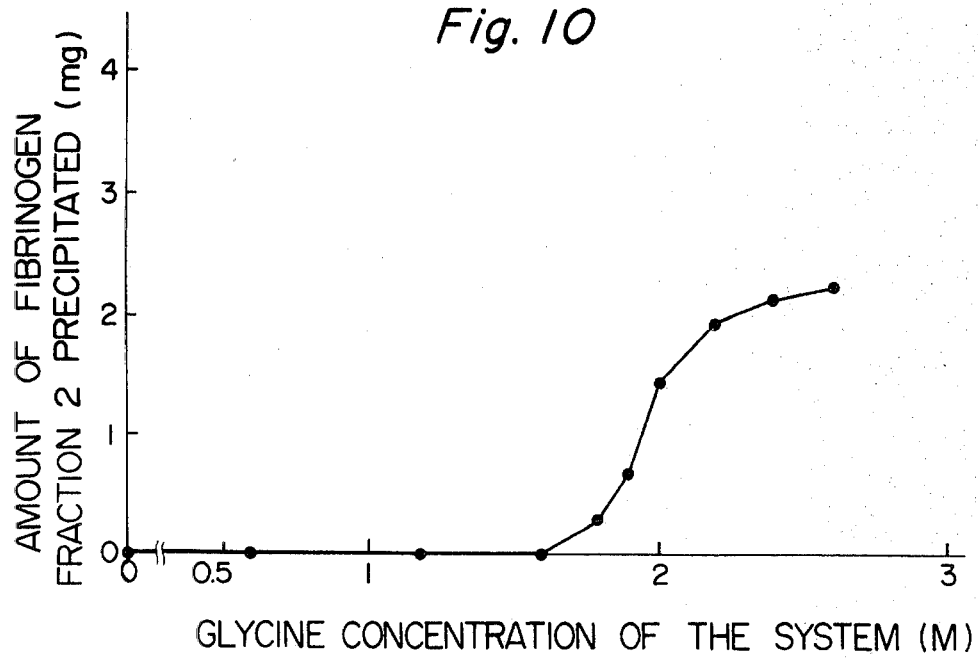

FIG. 10 shows the relation between the amount of fibrinogen fraction 2 precipitated and the concentration of glycine which was determined in the same way as in the case of FIG. 4 by varying the concentration of glycine at an ionic strength of 1.6.

From the results shown in FIGS. 9 and 10, it is preferred to employ conditions such that the aminocarboxylic acid concentration of the system is about 1.5 to about 3 M, preferably about 1.7 to about 2.7 M.

As described hereinabove with reference to the attached FIGS. 1 to 10, a fibrinogen-containing composition is contacted with at least one aminocarboxylic acid of formula (I) in an aqueous medium in the presence of an ionic strength controlling agent having an ionic strength of a specified range which depends upon the type of fibrinogen or its constituent components to be obtained. Preferably, the contacting is carried out such that the system meets the aforesaid requirements for the pH and/or the aminocarboxylic acid concentration.

According to this invention, by utilizing the aforesaid method of obtaining fibrinogen or its constituent components, there is provided a method for determining fibrinogen or its constituent components with high accuracy, reliability and rapidity, which is useful for the diagnosis of liver diseases and diseases induced by coagulation disorders of blood. Some embodiments of this assay method are as follows:

EMBODIMENT (A)

A method for determining fibrinogen fraction 1 in plasma, which comprises (i) contacting plasma with an aqueous solution of at least one aminocarboxylic acid of general formula (I) in the presence of an ionic strength controlling agent capable of adjusting the ionic strength of the system to about 0.02 to less than 1, and (ii) determining the resulting insoluble matter composed of fibrinogen fraction 1 in the plasma by a nephelometric procedure, or separating the insoluble matter and determining the insoluble matter by a known fibrinogen assay method such as the thrombin time method or by a known protein assay method, such as the Folin-Lowry method, or its modification.

EMBODIMENT (B)

A method for determining fibrinogen in plasma, which comprises (i) contacting plasma with an aqueous solution of at least one aminocarboxylic acid of formula (I) in the presence of an ionic strength controlling agent capable of adjusting the ionic strength of the system to 1 to about 2.2, and (ii) determining the resulting insoluble matter composed of fibrinogen in the plasma by a nephelometric procedure, or separating the insoluble matter and determining it by a known fibrinogen assay method such as the thrombin time method or by a known protein assay method, such as the Folin-Lowry method, or its modification.

EMBODIMENT (C)

A method for determining fibrinogen fraction 2 in plasma, which comprises (i) adjusting the ionic strength of the residue left after the separation of the insoluble matter in Embodiment (A), (i) to about 1.1 to about 1.6 with an ionic strength controlling agent, and (ii) determining the resulting insoluble matter composed of fibrinogen fraction 2 in the plasma by a nephelometric method, or separating the insoluble matter and determining it by a known fibrinogen assay method such as the thrombin time method or a known protein assay method, such as the Folin-Lowry method, or its modification.

In the Embodiments (A),(B) and (C), the insoluble matter to be determined can be formed in the same way as above with regard to the method of obtaining fibrinogen or its constituent components. When the insoluble matter contains non-clottable proteins, it is possible to set a corrected amount of fibrinogen or its constituent components experimentally depending upon non-clottable proteins present, and to correct the measured amount of the insoluble matter according to the experimentally set corrected value. For example, the resulting insoluble matter as suspended in the aqueous medium may be determined by the nephelometric method. Or, as stated hereinabove, the insoluble matter is separated and recovered, and then determined by a known fibrinogen assay method such as the thrombin time method or a known protein determining method, such as Folin-Lowry method, or its modification.

The nephelometric method can be used in the following manner. For example, a solution containing the resulting insoluble matter is subjected to a device suitable for measuring the turbidity of the solution, for example a spectrophotometer, and the absorbance of the turbid solution is measured preferably at a wavelength of 340 nm. If desired, in order to perform the measurement with good accuracy, the solution may be diluted with water, a buffer, physiological saline, etc. prior to the determination.

Since the degree of turbidity correlates with the amount of fibrinogen, fibrinogen fraction 1 or fibrinogen fraction 2 in the plasma, the turbidity of a turbid solution obtained by operating in the same manner as above using a standard plasma is measured and a calibration curve is drawn. The amount of fibrinogen, fibrinogen fraction 1 or fibrinogen fraction 2 in the plasma can be easily obtained by examining the measured turbidity against the calibration curve.

Examples of the known protein assay method include the Folin-Lowry method, a weight method or an ultraviolet absorptiometric method.

When the aforesaid Folin-Lowry method is utilized, the determination can be performed in the following manner.

The resulting insoluble matter is separated and recovered by an ordinary solid-liquid separating procedure such as centrifugal separation or filtration. The insoluble matter is dissolved in an alkaline solution, and the tyrosine content of the solution is measured by the Folin-Lowry method [Lowry, O. H. et al.; J. Biol. Chem., 193, 265–275 (1951)] which is a colorimetric method, and fibrinogen or its constituent component is determined. If desired, prior to the dissolving of the separated insoluble matter in the alkaline solution, non-clottable proteins dissolved in the aqueous solution adhering to the insoluble matter after the solid-liquid separation may be removed by purifying procedures, for example by washing it with the aqueous solution of aminocarboxylic acid used to obtain the insoluble matter, or by dissolving the insoluble matter again in an aqueous medium and causing thrombin to act on the solution to selectively precipitate and separate fibrinogen or its constituent component.

The weight method can be utilized in the following manner. For example, the insoluble matter is separated and recovered in the same way as in the Folin-Lowry method, and then preferably by using such means as filtration under reduced pressure, a liquid material adhering to the insoluble matter is removed as fully as possible. Then, it is dried to a constant weight by an ordinary method for drying proteins. By measuring the weight of the dried material with a suitable weighing device, the content of fibrinogen or its constituent component can be known. When it is impossible to perform the drying completely, the water content of the dried material is measured by a suitable water content measuring method such as a dry weight reduction method or a Karl-Fischer method, and the weight of the dried product can be calculated as an anhydrous material by using the water content measured. When other materials than water, such as the aminocarboxylic acid, remain in the dried material, the amounts of such remaining materials are determined by a suitable method, and the content of fibrinogen or its component can be determined by subtracting the amounts of such remaining materials from the amount of the dried material.

The ultraviolet absorptiometric method can be performed in the following manner. For example, the insoluble matter is separated and recovered in the same way as in the case of the Folin-Lowry method, and then dissolved in an aqueous medium. Then, the absorbance in the ultraviolet region of the solution is measured. The absorbance is preferably measured at a wave-length of 280 nm. Prior to the above procedure, non-clottable proteins dissolved in the aqueous solution adhering to the separated insoluble matter may be removed as in the case of the Folin-Lowry method.

The thrombin time method and a fibrin nephelometric method can also be cited as a method for determining fibrinogen.

The thrombin time method can be used in the following manner. For example, the insoluble matter is separated and recovered by the same procedure as in the Folin-Lowry method, and then re-dissolved in an aqueous medium. Then, the solution is subjected to the Clauss thrombin-time method [Clauss, A: Acta Haemat., 17, 237–246, (1957)] to determine the content of fibrinogen, fibrinogen fraction 1 or fibrinogen fraction 2. To measure the thrombin time, all methods for measuring the blood coagulating time can be utilized.

The fibrin nephelometry can be used in the following manner. For example, the resulting insoluble matter is separated and recovered in the same way as in the Folin-Lowry method, and dissolved in an aqueous medium. The solution is subjected to the method of Ellis et al. using thrombin [Ellis, B. C. et al., J. Lab. Clin. Med., 58, 477–488 (1961)] or the method of Hershgold et al. using Reptilase (tradename for a product of Abbott Co.) [Hershgold, E. J. et al., A. J. C. P., 63, 231–236 (1975)].

In the present invention, the residue left after the separation of fibrinogen or its constituent components can be used as a sample for assaying FDP in plasma.

The significance and effect of FDP are described below.

FDP is a generic term for degradation products of fibrin and fibrinogen formed by the fibrinolytic action of plasmin. It is said that these degradation products have an important bearing on DIC syndrome, thrombosis and hemorrhagic diseases attributed to derangement of the coagulation-fibrinolysis system of blood, bacterial infections, cancer, liver diseases and kidney diseases. FDP includes fragment X (molecular weight about 260,000) and fragment Y (molecular weight about 160,000) which are called early-stage FDP, and fragment D (molecular weight about 85,000) and fragment E (molecular weight about 57,000) which are called late-stage FDP, when classified according to the progress of fibrinolysis. They have an action of inhibiting thrombin or an action of inhibiting the polymerization of fibrin monomer. Fragments X and Y are receiving particular attention because their inhibiting actions are strong. Assay of these fragments is a useful means for the diagnosis of the aforesaid diseases.

FDP is currently determined in many cases by various immunological methods which involve the utilization of the property of FDP to react with an antifibrinogen antibody, and serum is usually used as an assay sample. Fragment X, an early-stage FDP, does not exist in serum because most of it is clotted by thrombin. The FDP level determined by using the serum is therefore lower than the actual total FDP level in the blood, thus causing a large error.

When fibrinogen is to be removed from plasma in accordance with this invention, fibrinogen can be separated from fragment X more sharply. Hence, the residue contains more fragment X than in conventional serum samples, and is quite free from fibrinogen.

Accordingly, by utilizing the residue resulting from the separation of fibrinogen or its components as a sample for assaying FDP, an FDP level in the blood closer to the true FDP level can be detected, and it is conducive to the early diagnosis of fibrinolytic disorders. Some embodiments of FDP assay using the aforesaid sample are described below.

EMBODIMENT (A)

An insoluble material composed of fibrinogen which is formed by contacting plasma with an aqueous solution of at least one aminocarboxylic acid of formula (I) in the presence of an ionic strength controlling agent capable of adjusting the ionic strength of the system to 1 to about 2.2 is separated and removed from the system by a known separating method such as centrifugal separation or filtration. The residue is diluted or concentrated after, if desired, purifying it by, for example, dialysis. Then, the FDP content of the prepared sample is determined by known immunological FDP assay methods such as the latex agglutination reaction (Gravey, M. B. and Black, J. M.: J. Clin. Pathol., 25, 680–682, 1972), and the erythrocyte agglutination inhibition reaction (Michio Fujimaki, Shojiro Ikematsu and Yuriko Baba: Blood and Vessels 5, 1015–1020, 1974), and other known FDP assay methods such as the Streptococcus agglutination test (Kaneo Yamada, Zenzaburo Yamada, Natsuhei Nakazawa, Takashi Meguro: Clinical Blood 13, 411–414, 1972).

EMBODIMENT (B)

Plasma is contacted with an aqueous solution of at least one aminocarboxylic acid of formula (I) in the presence of an ionic strength controlling agent capable of adjusting the ionic strength of the system to about 0.02 to less than 1. The resulting insoluble matter composed of fibrinogen fraction 1 is separated and removed from the system by a known separating method such as centrifugal separation or filtration. An ionic strength controlling agent is added to the residue to adjust its ionic strength to about 1.1 to about 1.6, and the resulting insoluble matter composed of fibrinogen reaction 2 is separated and removed by the same operation as in the case of separating fibrinogen fraction 1. The resulting residue is diluted or concentrated after, if desired, it is purified by such a method as dialysis. The FDP content of the residue can then be determined by the known methods described with regard to Embodiment (A).

According to this invention, there is also provided a reagent for obtaining or determining fibrinogen or its constituent components in an aqueous solution containing fibrinogen, said reagent comprising at least one aminocarboxylic acid of formula (I) and an ionic strength controlling agent. The reagent can be used advantageously both for separating fibrinogen or its constituent components and for determining fibrinogen or its constituent components in plasma. It should be understood therefore that the term "reagent" in this invention also includes diagnostic agents for the diagnosis of liver diseases and diseases attributed to the coagulation disorders of blood.

Preferably, the reagent contains an ionic strength controlling agent of such a type and in such an amount as will adjust the ionic strength of the system to the value described hereinabove with regard to the method of obtaining fibrinogen or its constituent components at the time of contact of a fibrinogen-contaning aqueous solution with the reagent. Furthermore, the reagent in accordance with this invention contains at least one aminocarboxylic acid selected from the group consisting of, for example, glycine, $\beta$-alanine and $\gamma$-aminobutyric acid in such an amount as will provide the aforesaid concentration in the system at the time of contacting of the fibrinogen-containing aqueous solution with the reagent. Of course, the reagent may be in a concentrated form which can be diluted suitably with an aqueous medium prior to use.

The reagent may be in the form of a liquid or solid. For example, it may be an aqueous solution containing at least one aminocarboxylic acid of formula (I) and an ionic strength controlling agent, or it may be a powder containing the two components in powder form. Or it may be in other solid forms such as granules, pellets, tablets and flakes. Alternatively, it may be a kit composed of a set of two components which are separately or simultaneously in a liquid or solid form. A reagent for diagnosis is preferably in such a form that fibrinogen or its constituent component in a predetermined amount of a plasma sample can be immediately determined by dissolving a predetermined amount of a solid reagent (e.g., tablets) or a liquid reagent (e.g., solution in an ampoule).

The above and many other similar embodiments are obvious to those skilled in the art, and are within the category of the reagent of this invention.

If desired, the above reagent of this invention may comprise a pH controlling agent, an antiseptic, a stabilizer and other auxiliary agents. The pH controlling agent is advantageously of such a type and in such an amount as will adjust the pH of the system to the aforesaid preferred pH range when the reagent is contacted with the plasma sample. Examples of the pH controlling agent include acids such as hydrochloric acid, sulfuric acid, phosphoric acid, acetic acid and citric acid; alkalies such as sodium hydroxide, potassium hydroxide, ammonium hydroxide, sodium hydrogen carbonate and sodium carbonate; and buffers such as acetic acid-sodium acetate, phosphoric acid-sodium phosphate, citric acid-sodium citrate, and hydrochloric acid-barbital sodium.

Examples of the antiseptic are sodium azide, benzoic acid, benzoic acid salts, phenol and sodium merthiolate.

The stabilizer includes, for example, Triton-X (a trademark for a product of Rohm & Haas Co.) and polyethylene glycol.

The following Examples further illustrate the present invention specifically. It should be understood that these examples are merely illustrative, and various changes and modifications are possible within the scope of this invention as described hereinabove and in the appended claims.

EXAMPLE 1

To 150 ml of citrated human plasma was added with stirring 1.5 liters of a 2.1 M aqueous solution of glycine (pH 6.2) whose ionic strength had been adjusted to 0.1 with sodium chloride, and the mixture was allowed to stand at 25° C. for 15 minutes. Then, the resulting precipitate was collected by filtration through a glass filter. The precipitate was washed with 50 ml of an aqueous solution of glycine (2.1 M, ionic strength=0.1, pH 6.2). The precipitate washed was then dissolved in 35 ml of a phosphate buffer having a pH of 7.4 and an ionic strength of 0.15, and 350 ml of the aforesaid glycine solution (2.1 M, ionic strength=0.1, pH 6.2) was added gradually with stirring. The mixture was allowed to stand at 25° C. for 15 minutes. The precipitate was collected by filtration, and again dissolved in 35 ml of a phosphate buffer having a pH of 7.4 and an ionic strength of 0.15 and containing 0.01 M of trans-p-aminomethylcyclohexanecarboxylic acid (AMCHA). The solution was dialyzed against 500 ml of a phosphate buffer (containing 0.1 M AMCHA, pH 7.4, ionic strength=0.15) for 24 hours using a Visking dialysis tube, and then lyophilized to afford 102 mg of a white powder.

SDS-polyacrylamide gel electrophoresis of the resulting powder showed that it consisted solely of fibrinogen fraction 1.

EXAMPLE 2

To 20 ml of human ACD plasma was gradually added 200 ml of a 2.8 M aqueous solution of $\gamma$-aminobutyric acid whose ionic strength had been adjusted to 0.3 and whose pH had been adjusted to 6.5 with a phosphate buffer. The mixture was allowed to stand at 20° C. for 15 minutes, and then centrifuged for 15 minutes at a speed of 3,500 rpm. The supernatant liquid was removed by decantation. The precipitate was washed twice with 5 ml of the aforesaid aqueous γ-aminobutyric acid solution, and dried at 30° C. under reduced pressure to afford 23 mg of a dried product.

SDS-polyacrylamide gel electrophoresis of the resulting product showed that it consisted solely of fibrinogen fraction 1.

EXAMPLE 3

One gram of human fibrinogen (Grade L; a product of Kabi Company) was dissolved in 100 ml of water. To the resulting aqueous solution was gradually added 100 ml of a 2.25 M aqueous solution of β-alanine whose ionic strength had been adjusted to 0.2 with potassium chloride and whose pH had been adjusted to 6.5 with sodium hydroxide. The mixture was maintained at 15° C. for 15 minutes. The resulting insoluble matter was centrifuged for 15 minutes at a speed of 10,000 rpm. The supernatant liquid was removed by decantation, and the insoluble matter was washed twice with 20 ml of the same β-alanine solution as described above, dissolved in 100 ml of physiological saline, and then stored in the frozen state. By the Folin-Lowry method, the yield of fibrinogen fraction 1 was determined to be 310 mg. In SDS-polyacrylamide gel electrophoresis, the fibrinogen fraction 1 thus obtained showed a single band.

EXAMPLE 4

350 mg of human fibrinogen (Grade L, a product of Kabi Company) was dissolved in 35 ml of water. To the solution was added gradually 350 ml of a 2.5 M aqueous solution of β-alanine whose ionic strength had been adjusted to 0.2 with ammonium chloride. The mixture was maintained at 25° C. for 15 minutes. Sodium chloride (25.6 g) was added to the supernatant liquid left after the removal of the insoluble matter. The resulting insoluble matter was collected by centrifugation at 10,000 rpm for 15 minutes, and washed with 10 ml of a 2.5 M aqueous solution of β-alanine having an ionic strength of 1.5 and a pH of 6.5. The washed insoluble matter was dissolved in a phosphate buffer having a pH of 7.4 and an ionic strength of 0.2, and lyophilized to afford 66 mg of a dried product.

SDS-polyacrylamide gel electrophoresis of the product showed that it consisted solely of fibrinogen fraction 2.

EXAMPLE 5

Sodium acetate was added to 50 ml of heparinized human plasma to adjust its ionic strength to 2.6. Then, 100 ml of a 3.5 M aqueous solution or γ-aminobutyric acid having a pH of 6.3 was added, and the mixture was allowed to stand at 20° C. for 30 minutes. The resulting insoluble matter was separated by centrifuging the mixture at 3,000 rpm for 15 minutes. The insoluble matter was dissolved in 10 ml of physiological saline, and the ionic strength of the solution was adjusted to 0.2 with ammonium sulfate. Then, 100 ml of a 2.3 M aqueous solution of glycine having a pH of 6.5 was added, and the resulting insoluble matter was removed by centrifugation. To the supernatant liquid was added 8.36 g of sodium chloride. The resulting mixture was allowed to stand at 20° C. for 15 minutes, and the precipitated fibrinogen fraction 2 was collected. The yield was 20 mg.

The fibrinogen fraction 2 so obtained showed a single band in SDS-polyacrylamide gel electrophoresis.

EXAMPLE 6

Fifty (50) milliliters of a 2.3 M aqueous solution of glycine (pH 6.0) whose ionic strength had been adjusted to 1.4 with sodium chloride was added to 10 ml of citrated human plasma, and they were mixed. The mixture was allowed to stand at 25° C. for 5 minutes, and centrifuged for 15 minutes at a speed of 3,500 rpm. The supernatant liquid was removed, and the precipitate was mixed well with 50 ml of the same aqueous glycine solution as described above. The mixture was centrifuged at a speed of 3,500 rpm for 15 minutes to separate the precipitate. The clottability of the resulting fibrinogen was 92%.

EXAMPLE 7

Commercially available human fibrinogen having a clottability of 55% was dissolved in water to form an aqueous solution containing fibrinogen in a concentration of 600 mg/dl. Two hundred (200) milliliters of a 2.5 M aqueous solution of β-alanine (pH 6.0) whose ionic strength had been adjusted to 1.4 with sodium chloride was added to 10 ml of the aqueous fibrinogen solution, and they were mixed. After standing at 37° C. for 10 minutes, the mixture was centrifuged at 3,500 rpm for 15 minutes. The supernatant liquid was removed. The precipitate was washed with 100 ml of the same aqueous β-alanine solution, and centrifuged for 15 minutes at 3,500 rpm. The clottability of the resulting fibrinogen was 96%.

EXAMPLE 8

To 50 ml of heparinized human plasma was added 250 ml of a 2.8 M aqueous solution of γ-aminobutyric acid (pH 6.1) whose ionic strength had been adjusted to 1.5 with potassium chloride, and they were well mixed. The mixture was allowed to stand at 25° C. for 10 minutes, and filtered to collect a precipitate. The precipitate was dissolved in 50 ml of water, and 250 ml of the same aqueous solution of γ-aminobutyric acid as described above was added. They were well mixed, and the mixture was allowed to stand for 10 minutes at 25° C. It was then filtered to afford a precipitate. The precipitate was dissolved in about 10 ml of water, and dialyzed against physiological saline at 5° C. overnight in a Visking cellophane tube, and then lyophilized. The resulting dried powder contained 75 mg of fibrinogen (as determined by the Folin-Lowry method). Its clottability was 93%.

EXAMPLE 9

Glycine (172.6 g), 5.84 g of sodium chloride, 1.05 g of potassium phosphate, monobasic and 4.37 g of sodium phosphate, dibasic were dissolved in distilled water to adjust the total volume to 1,000 ml (assay reagent).

Plasma-like sample solutions having varying contents of fibrinogen fraction 1 were prepared by adding varying amounts of the fibrinogen fraction 1 obtained in Example 3 and 60 mg/dl of the fibrinogen fraction 2 obtained in Example 4 to human serum. Each of these sample solutions in an amount of 0.2 ml was added to 2.0 ml of the assay reagent prepared as above, and the mixture was allowed to stand at room temperature for 3 minutes. Then, the absorbance of the solution at 340 nm was measured. The results are shown in Table 1.

TABLE 1

| Content of fibrinogen fraction 1 (mg/dl) | Absorbance at 340 nm |
|---|---|
| 50 | 0.065 |
| 100 | 0.135 |
| 200 | 0.270 |
| 400 | 0.540 |
| 600 | 0.810 |
| 800 | 1.08 |

A calibration line, plotted on the basis of the measured values, showed a linear relationship.

The turbid solution after the measurement of turbidity was centrifuged for 15 minutes at a speed of 10,000 rpm. The resulting supernatant liquid and precipitate were analyzed by SDS polyacrylamide gel electrophoresis. It was found that the precipitate contained only fibrinogen fraction 1 and the supernatant liquid was completely free from fibrinogen fraction 1.

EXAMPLE 10

$\beta$-Alanine (222.7 g) and 111.8 g of potassium chloride were dissolved in distilled water to form 1,000 ml of a solution. Using it as an assay reagent, fibrinogen fraction 2 was determined.

Plasma-like sample solutions of varying contents of fibrinogen fraction 2 were prepared by mixing varying amounts of the fibrinogen fraction 2 obtained in Example 5 and 150 mg/dl of the fibrinogen fraction 1 obtained in Example 1 with human plasma. Each of these sample solutions in an amount of 0.8 ml was added to 8.0 ml of the assay reagent prepared as above. The mixture was allowed to stand at 25° C. for 3 minutes, and centrifuged at 10,000 rpm for 15 minutes. The precipitate was collected and washed twice with 3 ml of the above assay reagent. Then, 2.5 N sodium hydroxide was added to dissolve the precipitate, and the amount of protein in the precipitate was determined by the Folin-Lowry method. By subtracting the amount of the added fibrogen fraction 1 from the determined value, the amount of fibrinogen fraction 2 was obtained.

The results are shown in Table 2.

TABLE 2

| Amount of fibrinogen fraction added (mg/dl) | Content of fibrinogen fraction 2 determined by the Folin-Lowry method (mg/dl) |
|---|---|
| 50 | 48 |
| 100 | 102 |
| 150 | 145 |
| 200 | 201 |
| 250 | 248 |
| 300 | 300 |

Fibrinogen fraction 2 added showed a recovery ratio of nearly 100% in any amounts when the $\beta$-alanine-precipitated protein was determined by the Folin-Lowry method.

EXAMPLE 11

To 2.0 ml of a 2.3 M aqueous solution of glycine whose ionic strength had been adjusted to 1.4 with sodium chloride was added 0.2 ml of each of various plasma samples having varying amounts of fibrinogen which had been determined by the tyrosine method (Izumi Kanai and Masamitsu Kanai, ed., Essentials of Clinical Testing Methods, 25th edition, VII-24). The mixture was allowed to stand at 25° C. for 3 minutes, and the absorbance was measured at a wavelength of 340 nm.

Figure 11:
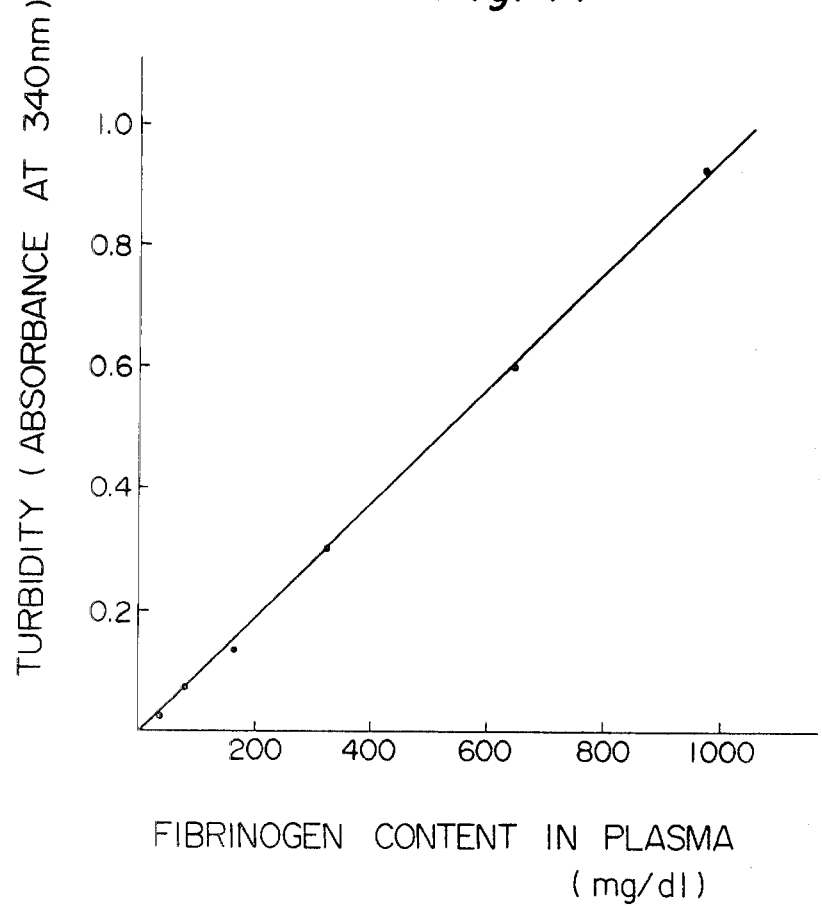

As a blank test, 2.0 ml of sodium chloride having an ionic strength of 1.4 was added to 0.2 ml of each of the various plasma samples described above, and the absorbance of the solution was measured by the same operation as in the case of using the aqueous glycine solution. For each of the various plasmas of varying concentrations, the difference obtained by subtracting the absorbance in the blank test from the absorbance caused by the aqueous glycine solution was plotted on the axis of ordinates, and the fibrinogen content (mg/dl), on the axis of abscissas to draw a calibration line which is shown in FIG. 11 of the attached drawings. According to FIG. 11, the relation shows linearity within a fibrinogen content of 0 to 1,000 mg/dl.

Ten assay samples of ACD plasma taken from eight human subjects were determined for fibrinogen content by a nephelometric method using an aqueous glycine solution under the same experimental conditions as described above and also by the tyrosine method. The results are shown in Table 3, and FIG. 12.

TABLE 3

| | Fibrinogen content (mg/dl) | |
|---|---|---|
| Assay sample No. | Method of the invention | Tyrosine method |
| 1 | 218 | 224 |
| 2 | 195 | 194 |
| 3 | 230 | 229 |
| 4 | 378 | 365 |
| 5 | 271 | 249 |
| 6 | 312 | 293 |
| 7 | 298 | 326 |
| 8 | 102 | 120 |

Figure 12:
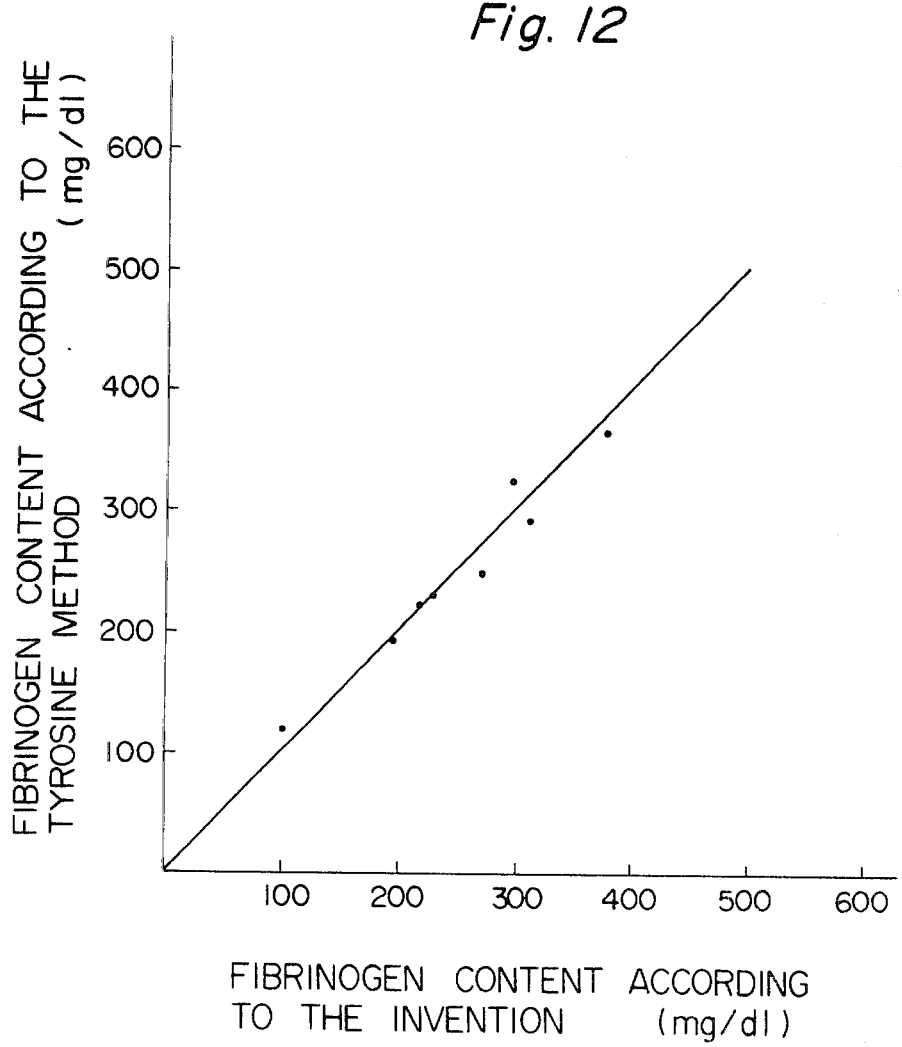

Based on the results shown in Table 3 and FIG. 12, the correlation between the values determined by the method of this invention (nephelometry) and those determined by the tyrosine method was examined. Consequently, a high correlation represented by a correlation coefficient $\gamma$ of 0.980 was noted.

EXAMPLE 12

Each of three plasma samples having different fibrinogen contents was added in an amount of 0.2 ml to a 2.5 M aqueous solution (2.0 ml) of $\beta$-alanine whose ionic strength had been adjusted to 1.4 with potassium chloride. The mixture was allowed to stand at 25° C. for 3 minutes, and as stated in Example 11, its fibrinogen content was determined by the method of this invention (by nephelometry) as described in Example 11.

Separately, the same three plasma samples were determined for fibrinogen content by ammonium sulfate nephelometry (Parfentjev. I. A. et al, Arch. Biochem., 46: 470, 1953).

By the two methods described above, the measurement was repeated 10 times for each plasma sample. The results are shown in Table 4.

The results show that the measuring accuracy by the method of this invention (nephelometry) is better than that of the ammonium sulfate nephelometry.

TABLE 4

| | Fibrinogen content in plasma (mg/dl) | | | | | |
| --- | --- | --- | --- | --- | --- | --- |
| | Method of the invention | | | Ammonium sulfate nephelometry | | |
| Plasma Measurement | A | B | C | A | B | C |
| 1 | 114 | 307 | 668 | 106 | 305 | 654 |
| 2 | 99 | 295 | 637 | 108 | 279 | 620 |
| 3 | 94 | 297 | 648 | 108 | 284 | 657 |
| 4 | 108 | 280 | 637 | 134 | 302 | 637 |
| 5 | 106 | 301 | 660 | 121 | 309 | 672 |
| 6 | 96 | 308 | 683 | 98 | 315 | 664 |
| 7 | 104 | 292 | 657 | 118 | 307 | 647 |
| 8 | 96 | 289 | 655 | 98 | 300 | 624 |
| 9 | 97 | 293 | 655 | 109 | 304 | 661 |
| 10 | 100 | 291 | 643 | 114 | 300 | 693 |
| Average | 101.4 | 297.3 | 654.3 | 111.4 | 300.5 | 652.9 |
| S. D | 6.4 | 8.4 | 14.2 | 10.9 | 11.0 | 22.1 |
| CV (%) | 6.3 | 2.8 | 2.2 | 9.8 | 3.7 | 3.4 |

EXAMPLE 13

A solution having an artificially prepared fibrilolysis state by the method described below was prepared as an FDP-containing assay solution. FDP was determined using this sample solution.

To 5 ml of an aqueous solution of human fibrinogen (Grade L; a product of Kabi Company) (containing 900 mg/dl of fibrinogen) was added 0.2 ml of urokinase 24,000 U/ml, and they were incubated at 37° C. for 15 minutes. Then, 5 ml of a 0.1 M aqueous solution of trans-p-aminomethylcyclocarboxylic acid and Trasylol (2500 KIU) as an anti-plasmin agent were added.

To 1 ml of the resulting solution was added 10 ml of a 2.3 M aqueous solution of glycine (pH 6.0) whose ionic strength had been adjusted to 1.5 with sodium chloride, and the mixture was allowed to stand at 20° C. for 10 minutes. The resulting insoluble matter composed of fibrinogen was removed by centrifugation at 10,000 rpm for 15 minutes. 0.1 ml of the resulting supernatant was taken, and diluted to various concentrations using "FDPL test ®" (a latex reagent kit for FDP assay, a product of Teikoku Hormone Mfg., Co., Ltd.). The FDP content was determined by examining agglutination reactions. A part of the supernatant liquid was taken, and analyzed by SDS-polyacrylamide gel electrophoresis.

Separately, 1 ml of the assay solution was diluted with 10 ml of physiological saline, and 40 units of thrombin was added and incubated at 37° C. for 1 hour. The resulting fibrin was removed by centrifugation for 12 minutes at 3,000 rmp. 0.1 ml of the resulting supernatant liquid was taken, and its FDP content was determined using "FDPL test ®" in the same way as above. Furthermore, a part of the supernatant liquid was taken, and subjected to electrophoresis in the same way as above.

The samples prepared by the above two methods had the following FDP contents.

TABLE 5

| Sample | FDP content (μg/ml) |
| --- | --- |
| Sample obtained by the invention | 120 |
| Sample obtained by treatment with thrombin | 40 |

Figure 13:
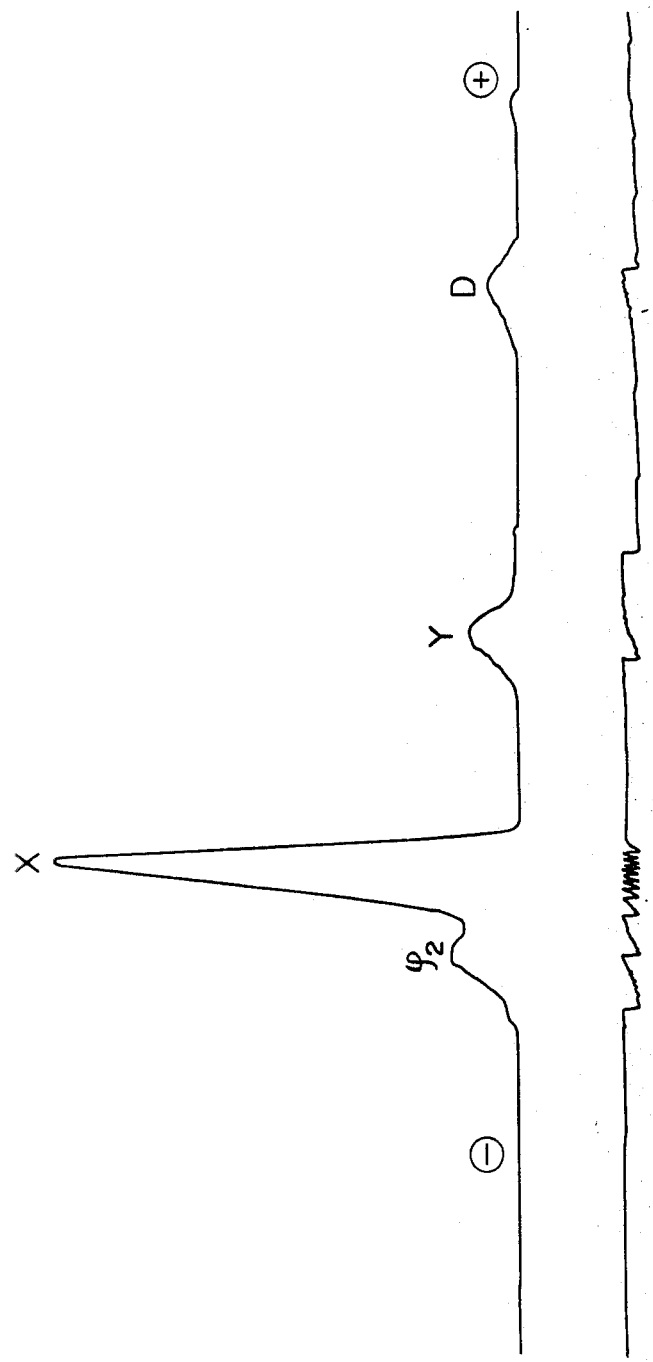
Figure 14:
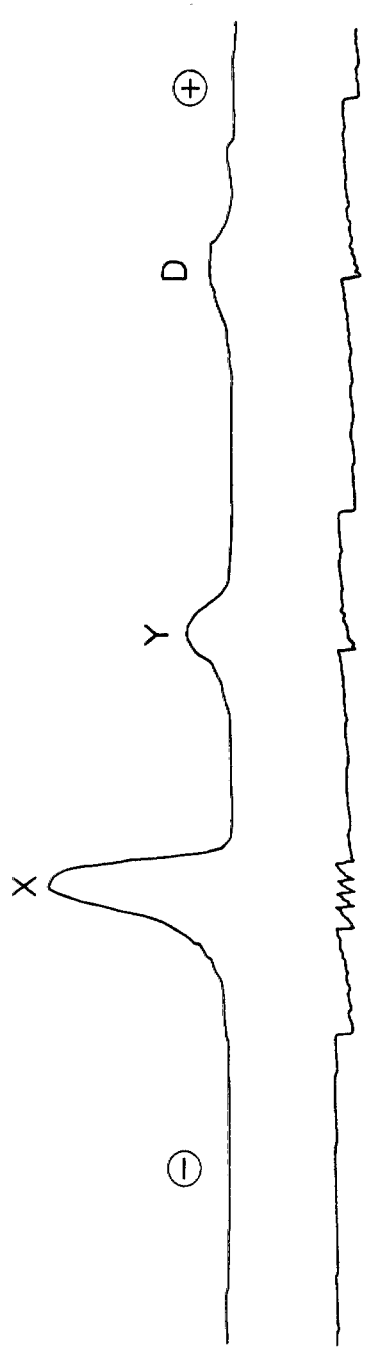
Figure 15:
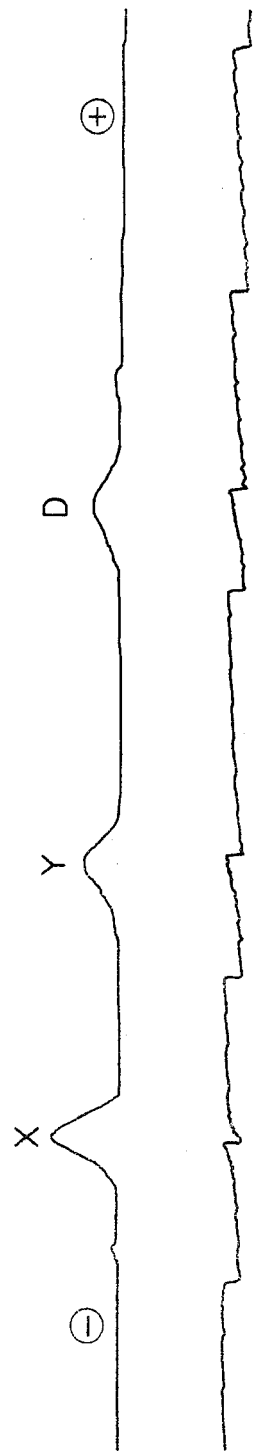

The densitograms obtained are shown in FIG. 13 (the assay solution), FIG. 14 (the sample obtained by the method of this invention), and FIG. 15 (the sample obtained by treatment with thrombin).

The results of determination demonstrate that with the sample obtained by the method of this invention, about three times as high an FDP level as in the case of the sample obtained by treatment with thrombin was detected.

As shown in the densitogram of FIG. 14, the sample obtained by the method of this invention hardly contains fibrinogen. As is clearly seen from FIGS. 14 and 15, the content of fragment X in the sample obtained by the method of this invention is evidently higher than that of the sample obtained by treatment with thrombin and is close to the total FDP level in the assay solution shown in FIG. 13.

EXAMPLE 14

To 0.2 ml of the same assay solution as used in Example 13 was added 2.0 ml of a 2.5 M aqueous solution of β-alanine (pH 6.0) whose ionic strength was adjusted to 0.2 with sodium chloride. The mixture was allowed to stand for 10 minutes at 20° C. The resulting insoluble matter composed of fibrinogen was removed by centrifugation at 10,000 rpm for 15 minutes. A powder of sodium chloride was dissolved in the resulting supernatant liquid to adjust its ionic strength to 1.5. The solution was allowed to stand at 20° C. for 30 minutes, and centrifuged at 10,000 rpm for 15 minutes to remove the precipitate. 0.1 ml of the resulting residue was diluted to various concentrations, and the FDP content was determined using an erythrocyte agglutination inhibiting reaction reagent kit (a product of Wellcome Company). As a result, the FDP content of the assay solution was 50 μg/ml which well corresponded with the value determined in Example 13.

EXAMPLE 15

Glycine (172.6 g), 85.6 g of ammonium chloride and 0.3 g of benzoic acid were added to distilled water to form 1,000 ml of an aqueous solution. Two milliliters of the solution for single application was placed in each of sealable containers to form a reagent for determining fibrinogen.

EXAMPLE 16

β-Alanine (222.7 g), 115.6 g of sodium acetate, 1.0 g of Triton-X and 0.025 g of sodium merthiolate were dissolved in distilled water to form about 900 ml of an aqueous solution. The pH of the aqueous solution was adjusted to 6.3 with dilute hydrochloric acid. The solution was diluted with distilled water to a volume of 1,000 ml. The resulting solution was placed as 5 ml portions into ampoules and the ampoules were sealed up. The reagent can be used for the determination of fibrinogen.

EXAMPLE 17

Glycine (172.6 g), 5.84 g of sodium chloride, 1.05 g of potassium phosphate (monobasic), 4.37 g of sodium phosphate (dibasic) and 1 g of sodium nitride were dissolved in water to form 1,000 ml of an aqueous solution. When, 2.0 ml of the resulting reagent was taken and 0.2 ml of citrated human plasma was added to it, fibrinogen fraction 1 could be determined.

EXAMPLE 18

β-Alanine (222.7 g) and 14.9 g of potassium chloride were finely divided by a pulverizer, and 1.20 g of the powdery mixture was weighed into a 5 ml-ampoule and sealed. It was dissolved in 5 ml of distilled water prior to use, and used for the determination of fibrinogen fraction 1.

What is claimed is:

1. A method for obtaining fibrinogen or its constituent components, which comprises contacting a fibrinogen-containing composition with at least one aminocarboxylic acid of the formula $$H_2N(CH_2)_nCO_2H \tag{I}$$

wherein n is a positive integer,
in an aqueous medium in the presence of an ionic strength controlling agent capable of adjusting the ionic strength of the system to from about 0.02 to about 2.2 to collect at least one member selected from the group consisting of fibrinogen fraction 1 and fibrinogen fraction 2.

2. A method according to claim 1 which comprises contacting a fibrinogen-containing composition with at least one aminocarboxylic acid of the following formula $$H_2N(CH_2)_nCO_2H \tag{I}$$

wherein n is a positive integer,
in an aqueous medium in the presence of an ionic strength controlling agent capable of adjusting the ionic strength of the system to 1 to about 2.2, thereby to separate and collect the resulting insoluble fibrinogen composed of fibrinogen fraction 1 and fibrinogen fraction 2.

3. A method according to claim 1 wherein n in said formula (I) is 1, 2 or 3.

4. A method according to claim 1 which comprises contacting a fibrinogen-containing composition with at least one aminocarboxylic acid of the formula $$H_2N(CH_2)_nCO_2H \tag{I}$$

wherein n is a positive integer,
in an aqueous medium in the presence of an ionic strength controlling agent capable of adjusting the ionic strength of the system to about 0.02 to less than 1, thereby to separate and collect the resulting insoluble fibrinogen fraction 1.

5. A method according to claim 4 wherein the ionic strength of the residue resulting after separation of the fibrinogen fraction 1 is adjusted to 1 to about 2.2, thereby to separate and collect the resulting insoluble fibrinogen fraction 2.

6. A method according to claim 4 wherein said fibrinogen-containing composition is the fibrinogen composed of fibrinogen fraction 1 and fibrinogen fraction 2 obtained in claim 2.

7. A method for determining fibrinogen fraction 1 in plasma, which comprises (i) contacting plasma with an aqueous solution of at least one aminocarboxylic acid of the formula $$H_2N(CH_2)_nCO_2H \tag{I}$$

wherein n is a positive integer,
in the presence of an ionic strength controlling agent capable of adjusting the ionic strength of the system to a value at which fibrinogen fraction 1 is precipitated, and (ii) determining the resulting insoluble matter composed of fibrinogen fraction 1 in the plasma.

8. A method according to claim 7 wherein n in formula (I) is 1, 2 or 3.

9. A method for determining fibrinogen fraction 1 in plasma according to claim 7, which comprises (i) contacting plasma with an aqueous solution of at least one aminocarboxylic acid of the formula $$H_2N(CH_2)_nCO_2H \tag{I}$$

wherein n is a positive integer,
in the presence of an ionic strength controlling agent capable of adjusting the ionic strength of the system to about 0.02 to less than 1, and (ii) determining the resulting insoluble matter composed of fibrinogen fraction 1 in the plasma.

10. A method for determining fibrinogen fraction 2 in plasma, which comprises (i) adjusting the ionic strength of the residue left after the separation of the insoluble matter formed in (i) in claim 9 with an ionic strength controlling agent to a value at which fibrinogen fraction 2 is precipitated, and (ii) determining the resulting insoluble matter composed of fibrinogen fraction 2 in the plasma.

11. A method for determining fibrinogen fraction 2 in plasma according to claim 10, which comprises (i) adjusting the ionic strength of the residue left after the separation of the insoluble matter formed in (i) of claim 9 to 1 to about 2.2 with an ionic strength controlling agent, and (ii) determining the resulting insoluble matter composed of fibrinogen fraction 2 in the plasma.

12. A method for determining fibrinogen in plasma which comprises (i) contacting plasma with an aqueous solution of at least one aminocarboxylic acid of the formula $$H_2N(CH_2)_nCO_2H \tag{I}$$

wherein n is a positive integer,
in the presence of an ionic strength controlling agent capable of adjusting the ionic strength of the system to 1 to about 2.2, and (ii) determining the resulting insoluble matter composed of fibrinogen in the plasma.

13. A method according to claim 12 wherein n in formula (I) is 1, 4 or 5.

14. A reagent for obtaining or determining fibrinogen or its constituent components in an aqueous solution containing fibrinogen, said reagent comprising at least one aminocarboxylic acid of the formula $$H_2N(CH_2)_nCO_2H \tag{I}$$

wherein n is a positive integer, and an ionic strength controlling agent capable of adjusting the ionic strength of the system to from about 0.02 to about 2.2.

* * * * *

UNITED STATES PATENT AND TRADEMARK OFFICE
CERTIFICATE OF CORRECTION

PATENT NO. : 4,295,855

DATED : October 20, 1981

INVENTOR(S) : Susumu Sasaki, Kyoji, Akio Koide

It is certified that error appears in the above—identified patent and that said Letters Patent is hereby corrected as shown below:

Claim 13, line 2 should read -- formula (I) is 1, 2 or 3. --

Signed and Sealed this

Thirteenth Day of April 1982

[SEAL]

Attest:

Attesting Officer

GERALD J. MOSSINGHOFF

Commissioner of Patents and Trademarks